US009572612B2

(12) United States Patent
Sengun et al.

(10) Patent No.: US 9,572,612 B2
(45) Date of Patent: Feb. 21, 2017

(54) METHODS AND DEVICES FOR ANCHORING A GRAFT TO BONE

(71) Applicant: DePuy Mitek, LLC, New Brunswick, NJ (US)

(72) Inventors: Mehmet Z. Sengun, Canton, MA (US); Eduard Grinberg, Sharon, MA (US); Michael S. Varieur, Portsmouth, RI (US); Dennis M. Burke, Mansfield, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 15/177,959

(22) Filed: Jun. 9, 2016

(65) Prior Publication Data
US 2016/0287304 A1    Oct. 6, 2016

Related U.S. Application Data

(62) Division of application No. 14/542,010, filed on Nov. 14, 2014, now Pat. No. 9,387,067, which is a division of application No. 13/489,070, filed on Jun. 5, 2012, now Pat. No. 8,915,961.

(51) Int. Cl.
*A61F 2/08* (2006.01)
*A61B 17/88* (2006.01)

(52) U.S. Cl.
CPC .................................. *A61B 17/8811* (2013.01)

(58) Field of Classification Search
CPC combination set(s) only.
See application file for complete search history.

(56) References Cited

U.S. PATENT DOCUMENTS

| | | | |
|---|---|---|---|
| 5,997,582 A | 12/1999 | Weiss | |
| 6,388,043 B1 | 5/2002 | Langer et al. | |
| 6,712,853 B2 | 3/2004 | Kuslich | |
| 7,628,800 B2 | 12/2009 | Sherman et al. | |
| 7,654,321 B2 | 2/2010 | Zazovsky et al. | |
| 7,850,711 B1 | 12/2010 | Stone et al. | |
| 8,915,961 B2 | 12/2014 | Sengun et al. | |
| 9,387,067 B2 | 7/2016 | Sengun et al. | |
| 2006/0293749 A1 | 12/2006 | Hudgins et al. | |
| 2007/0162122 A1 | 7/2007 | Whittaker | |
| 2009/0304773 A1 | 12/2009 | Milbocker et al. | |
| 2009/0312806 A1* | 12/2009 | Sherman | A61F 2/44 606/86 R |
| 2010/0111829 A1 | 5/2010 | Drapeau et al. | |
| 2010/0152851 A1 | 6/2010 | Linares | |
| 2010/0262188 A1 | 10/2010 | Rabiner et al. | |

* cited by examiner

Primary Examiner — Sameh Boles

(57) ABSTRACT

Methods and devices are provided for anchoring graft to bone. In one exemplary embodiment, a bone cavity is created in bone, a graft is partially advanced into the bone cavity, and a hardenable filler material is inserted into the cavity. The hardenable filler material can change from a viscous first state to a harder second state, compressing the graft against the walls of the bone cavity and thereby anchoring the graft within the cavity. The hardenable filler material can be inserted in an open sac, a closed sac, other carriers or housings, or directly into the bone cavity.

11 Claims, 5 Drawing Sheets

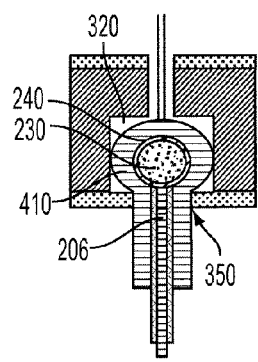
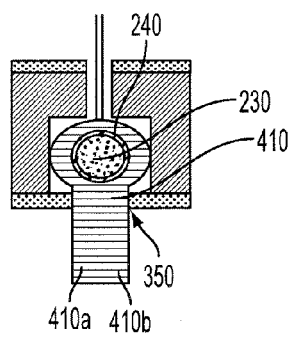
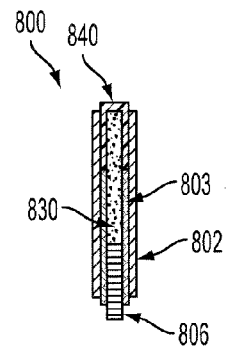
FIG. 6　　　FIG. 7　　　FIG. 8
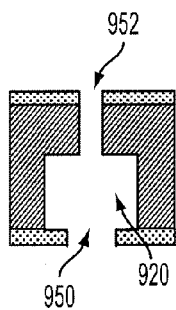
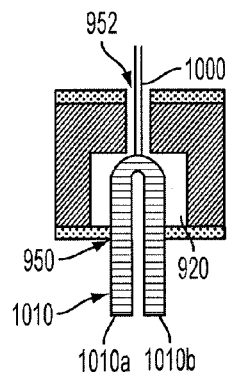
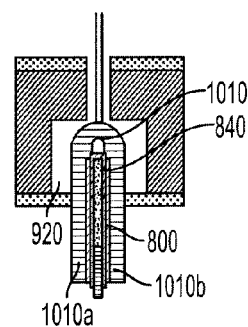
FIG. 9　　　FIG. 10　　　FIG. 11
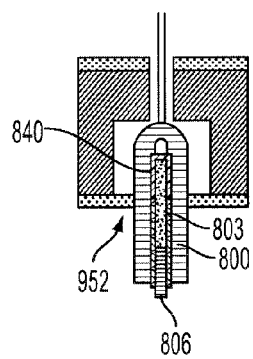
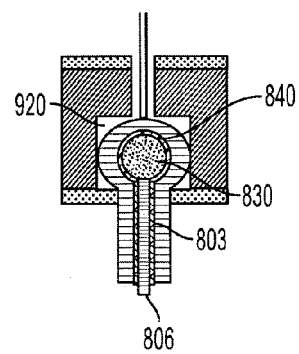
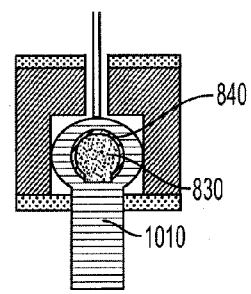
FIG. 12　　　FIG. 13　　　FIG. 14

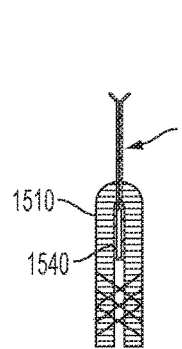 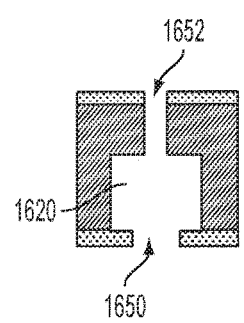 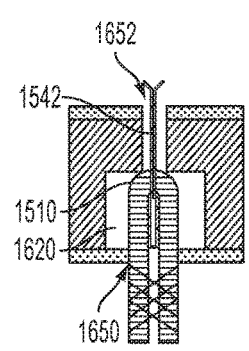 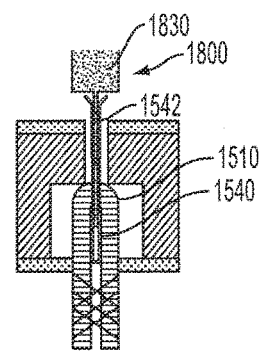
FIG. 15   FIG. 16   FIG. 17   FIG. 18
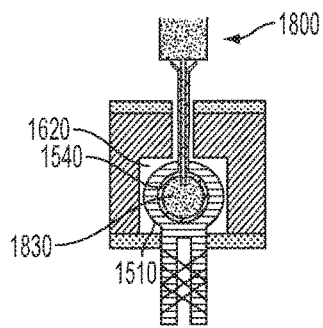 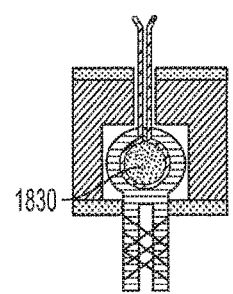 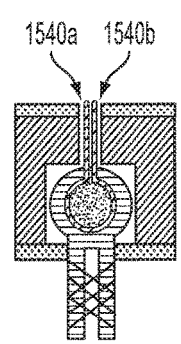
FIG. 19   FIG. 20   FIG. 21

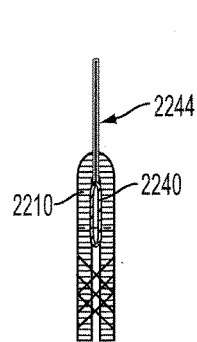 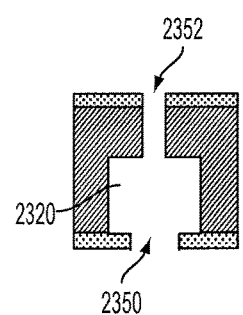 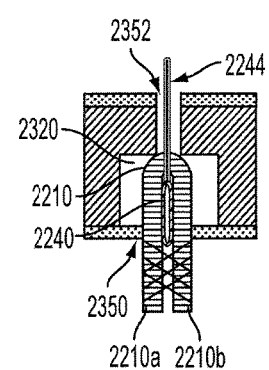 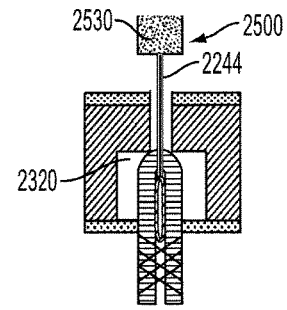
FIG. 22  FIG. 23  FIG. 24  FIG. 25
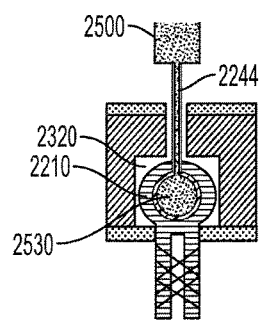 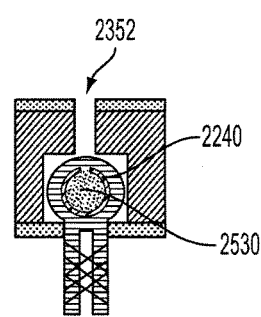
FIG. 26  FIG. 27

METHODS AND DEVICES FOR ANCHORING A GRAFT TO BONE

CROSS-REFERENCE TO RELATED APPLICATIONS

This application is a divisional of U.S. application Ser. No. 14/542,010 filed on Nov. 14, 2014, and entitled "Methods and Devices for Anchoring a Graft to Bone," which is a divisional of U.S. application Ser. No. 13/489,070 filed on Jun. 5, 2012, and entitled "Methods and Devices for Anchoring a Graft to Bone," which are hereby incorporated by reference herein in their entireties.

FIELD

The present invention relates generally to methods and devices for anchoring a graft to bone.

BACKGROUND

Joint injuries can result in the complete or partial detachment of ligaments, tendons and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full function to the injured joint. Numerous devices are currently available to re-attach soft tissue to bone. Examples of such currently available devices include screws, staples, suture anchors, and tacks.

Such procedures involve the re-attachment of the detached tissue using "traditional" attachment devices such as staples, sutures, and bone screws. Such traditional attachment devices have also been used to attach tendon or ligament grafts (often formed from autologous tissue harvested from elsewhere in the body) to the desired bone or bones. In soft tissue re-attachment procedures utilizing interference screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone. Although traditional attachment devices can hold soft tissue to bone, the devices can crack, break, or otherwise fail during or after implantation, which can delay healing and/or injure the patient. Additionally, the traditional attachment devices can damage the soft tissue and/or bone by being driven therein, which can cause undesirable effects, such as infection, delayed healing, and/or additional surgery to repair the device, the tissue, and/or the bone.

In procedures where a graft is held to the bone using an interference screw, such as ACL reconstruction, a bone tunnel is created that is just large enough to fit the graft. The graft is either pulled or pushed into the bone tunnel using various methods, and the interference screw is inserted into the bone tunnel. The interference fit of the shank and the head of the screw hold the graft against the bone inside the bone tunnel with a very high degree of interference. However, failure can occur due to screw breakage, bone or graft damage, and high torque requirements. In another approach, the graft can be pulled through a bone tunnel and suspended, e.g., with sutures or cords, from the other side of the bone. However, this approach does not provide aperture fixation and can lead to tunnel widening due to abrasion from the sutures or cords during movement.

Accordingly, there remains a need for improved methods and devices for anchoring a graft to bone.

SUMMARY

In one embodiment, a surgical method is provided that includes forming a cavity in bone, the cavity having a first maximum diameter, and forming a first access tunnel providing access into the cavity, the first access tunnel having a second maximum diameter that is less than the first maximum diameter. The method further includes advancing a graft into the cavity through the first access tunnel such that a first portion of the graft is positioned within the cavity, and a second portion of the graft extends out of the cavity. A hardenable filler material is inserted in a first state into the cavity, the hardenable filler material causing the first portion of the graft to contact and push against walls of the cavity such that when the hardenable filler material changes from the first state to a second, harder state, the first portion of the graft is prevented from exiting the cavity through the first access tunnel.

The method can vary in a number of ways. For example, the method can further include advancing a flexible sac into the cavity. The sac can be positioned in the cavity when the hardenable filler material is inserted into the cavity such that inserting hardenable filler material into the cavity causes the flexible sac to expand within the cavity. In other aspects, the hardenable filler material can be located within the flexible sac when the flexible sac and the hardenable filler material are inserted into the cavity. In another embodiment, the second portion of the graft can extend out of the cavity through the first access tunnel, the flexible sac can be advanced into the cavity through the first access tunnel, and the hardenable filler material can be inserted into the cavity through the first access tunnel.

The method can further include forming a second access tunnel providing access into the cavity. The second portion of the graft can extend out of the cavity through the first access tunnel, the flexible sac can be advanced into the cavity through the second access tunnel, and the hardenable filler material can be inserted into the cavity through the second access tunnel. Alternatively, the method can include forming a second access tunnel providing access into the cavity, and advancing the graft into the cavity through the first access tunnel can include pulling a cord coupled to the graft through the second access tunnel. The second portion of the graft can extend out of the cavity through the first access tunnel, the flexible sac can be advanced into the cavity through the first access tunnel, and the hardenable filler material can be inserted into the cavity through the first access tunnel. In some embodiments, the method can include forming a second access tunnel providing access into the cavity, wherein the second portion of the graft can extend out of the cavity through the first access tunnel, the flexible sac can be advanced into the cavity through the first access tunnel, and the hardenable filler material can be inserted into the cavity through the second access tunnel.

The method can include a variety of modifications. For example, the method can include forming a second access tunnel providing access into the cavity, and advancing the graft into the cavity through the first access tunnel can include pulling a cord coupled to the graft through the second access tunnel. The second portion of the graft can extend outside of the cavity through the first access tunnel, and the hardenable filler material can be inserted into the cavity through the first or the second access tunnel. In other aspects, the first maximum diameter of the cavity can be at least 20% greater than the second maximum diameter of the first access tunnel. Forming the cavity in bone can include forming the cavity entirely in cancellous bone, and forming the first access tunnel can include forming a tunnel through cortical bone adjacent the cancellous bone.

In another aspect, a surgical method is provided that includes advancing a graft into a cavity formed in bone, the graft being folded in the cavity such that opposed sides of the graft have an intermediate portion extending therebetween that define an internal pocket having a first size. A flexible sac can be advanced in an unexpanded configuration into the internal pocket in the cavity, and a hardenable filler material can be advanced in a first state into the internal pocket in the cavity, thereby causing the flexible sac to move from the unexpanded configuration to an expanded configuration, and causing the internal pocket to move from the first size to a second, larger size to cause the opposed sides and the intermediate portion of the graft to contact and push against walls of the cavity, such that when the hardenable filler material changes from the first state to a second, harder state in the internal pocket, the opposed sides and the intermediate portion of the graft are held in contact against the walls of the cavity.

In some embodiments, the flexible sac and the hardenable filler material can be simultaneously advanced into the internal pocket. In some embodiments, the flexible sac can be advanced into the internal pocket before the hardenable filler material is advanced into the internal pocket. The graft can be advanced into the cavity through a same access tunnel as the flexible sac and the hardenable filler material. In some embodiments, the graft and the flexible sac can be advanced into the cavity through a first access tunnel, and the hardenable fillable material can be advanced into the cavity through a second access tunnel. In some embodiments, the graft can be advanced into the cavity through a first access tunnel, and the flexible sac and the hardenable filler material can be advanced into the cavity through a second access tunnel.

In another aspect, a surgical kit is provided that includes a flexible sac and a hardenable filler material. The flexible sac has an unexpanded configuration and an expanded configuration. The flexible sac is configured to be advanced in the unexpanded configuration into an internal pocket of a graft that is positioned in a cavity formed in bone. The hardenable filler material has a first state and a second, harder state. The hardenable filler material is configured to be inserted in the first state into the flexible sac positioned in the internal pocket of the graft, thereby causing the flexible sac to move from the unexpanded configuration to the expanded configuration and causing the internal pocket to move from a first size to a second, larger size to cause the graft to contact and push against walls of the cavity such that when the hardenable filler material changes from the first state to the second, harder state in the internal pocket, the graft is held in contact against the walls of the cavity. The flexible sac and the hardenable filler material can be sterile.

The surgical kit can also include a delivery tool. The delivery tool can include a tube having an inner lumen, the flexible sac in the unexpanded configuration being disposed within the inner lumen, the hardenable filler material in the first state being disposed within the flexible sac disposed within the inner lumen, and the delivery tool being configured to advance the flexible sac having the hardenable filler material disposed therein from out of the inner lumen and into the internal pocket. In another embodiment, the delivery tool can have an inner lumen, the hardenable filler material being disposed within the inner lumen, and the delivery tool being configured to advance the hardenable filler material from out of the inner lumen and into the internal pocket having the flexible sac pre-disposed therein.

BRIEF DESCRIPTION OF THE DRAWINGS

The invention will be more fully understood from the following detailed description taken in conjunction with the accompanying drawings, in which:

FIG. 6 is a cross-sectional view of the sac of FIG. 5 delivered into the cavity;

FIG. 7 is a cross-sectional view of the sac of FIG. 5 delivered into the cavity after withdrawal of the delivery tool;

FIG. 8 is a cross-sectional view of another embodiment of a delivery tool;

FIG. 9 is cross-sectional view of another embodiment of a bone cavity;

FIG. 10 is a cross-sectional view of a graft partially inserted into the bone cavity of FIG. 9;

FIG. 11 is a cross-sectional view of a delivery tool loaded with a sac of hardenable filler material partially inserted into the graft of FIG. 10;

FIG. 12 is a cross-sectional view of the delivery tool of FIG. 11 with the outer tube removed;

FIG. 13 is a cross-sectional view of the sac of FIG. 11 delivered into the cavity;

FIG. 14 is a cross-sectional view of the sac of FIG. 11 delivered into the cavity after withdrawal of the delivery tool;

FIG. 15 is a cross-sectional view of an embodiment of an unfilled sac in a graft;

FIG. 16 is a cross-sectional view of a bone cavity;

FIG. 17 is a cross-sectional view of the graft and sac of FIG. 15 partially inserted into a bone cavity;

FIG. 18 is a cross-sectional view of a syringe filled with hardenable filler material partially inserted into the sac of FIG. 17;

FIG. 19 is a cross-sectional view of the hardenable filler material injected into the sac of FIG. 18;

FIG. 20 is a cross-sectional view of the sac of FIG. 19 after the syringe is removed;

FIG. 21 is a cross-sectional view of the sac of FIG. 20 after the ends of the sac are trimmed;

FIG. 22 is a cross-sectional view of an embodiment of an unfilled sac with a detachable tube in a graft;

FIG. 23 is a cross-sectional view of a bone cavity;

FIG. 24 is a cross-sectional view of the graft and sac of FIG. 22 partially inserted into a bone cavity, with the delivery tube extending therefrom;

FIG. 25 is a cross-sectional view of a syringe filled with hardenable filler material partially inserted into the delivery tube of FIG. 24;

FIG. 26 is a cross-sectional view of the hardenable filler material of FIG. 18 injected through the delivery tube into the sac;

FIG. 27 is a cross-sectional view of the sac of FIG. 26 filled with hardenable filler material after the delivery tube is removed;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for anchoring a graft to bone, such as in arthroscopic surgical procedure. In general, the methods and devices allow a graft to be fixed within a bone cavity by a hardenable filler material. In an exemplary embodiment, a bone cavity can be formed in bone, and a graft can be advanced such that a portion of the graft is positioned within the cavity. A hardenable filler material in a first state can be placed into the cavity, such that when the hardenable filler material changes from the first state to a second, harder state, it can hold the portion of the graft within the cavity against the bone, fixing it within the cavity. In an exemplary embodiment, the hardenable filler material, when in the second hardened state, has a size that is larger than a size of an access tunnel extending into the cavity such that the hardenable filler material, and thus the graft, are prevented from passing through the tunnel. As a result, the graft is securely retained within the cavity. The hardenable filler can be placed directly into the cavity or it can be placed within a separate sac. In embodiments in which a sac is used, the sac can be filled with the hardenable filler material either before or after the sac is advanced into the cavity. Fixation of the graft with a hardenable filler material can eliminate the need for fixation screws or other anchoring devices, and can reduce or eliminate bone and graft damage.

Figure 1:
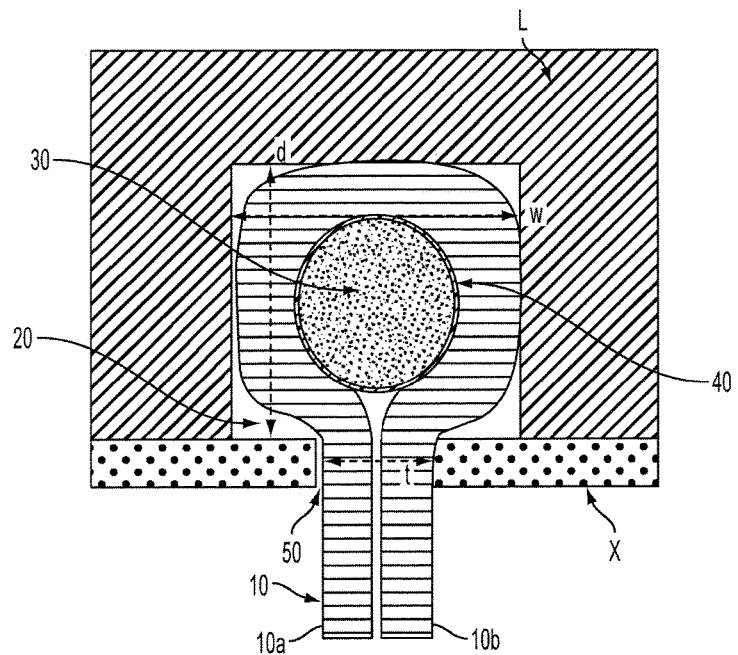
FIG. 1 is a cross-sectional view of one embodiment of a graft fixed in a bone cavity.

FIG. 1 illustrates one exemplary embodiment of a graft 10 fixed in a bone cavity 20 by hardenable filler material 30. This fixation can be accomplished by various methods, which will be discussed further below. While the hardenable filler material 30 in this embodiment is contained within a sac 40, the sac is optional, and in other embodiments the hardenable filler material can be placed directly into the cavity. The graft can be placed in the cavity in various ways, for example, as illustrated in FIG. 1, the graft 10 is partially placed in the cavity 20 with two ends or legs 10a, 10b of the graft 10 exiting the bone cavity 20 through an access tunnel 50.

The cavity 20 can have various shapes and sizes, but generally is formed within softer cancellous bone L. The cavity 20 can be formed by first creating an access tunnel 50 in the harder cortical bone X, and then creating a cavity within the cancellous bone L. Those of ordinary skill in the art will understand that various tools can be used to create a cavity having various sizes and shapes. FIG. 1 shows a single access tunnel 50 in the cortical bone X, but multiple access tunnels can be formed to the cavity through the cortical bone. In some embodiments, the access tunnels can extend through the cancellous bone, as well. The term "cavity" as used herein is intended to refer to an enlarged opening or hollow area within bone, while the term "tunnel" is used to refer to a smaller tract or pathway extending from a surface of the bone to the cavity. However, a person skilled in the art will appreciate that the tunnel and cavity can refer to different regions of the same pathway. For example, a single opening can be formed in bone, and a first part of the opening extending from the outer surface into the bone can be a tunnel, while the end or inner portion of the opening can be a cavity. As will be discussed in detail below, the dimensions of the tunnel and cavity can be the same or can differ.

As discussed above, the size and shape of the bone cavity can vary based on a number of factors, including, for example, the size of the bone or the size of the graft. As illustrated in FIG. 1, the bone cavity 20 has a width w sufficient to allow the graft 10 to be folded over within the cavity 20, and a depth d sufficient to allow the folded portion of the graft to be disposed therein. In an exemplary embodiment, the depth d is less than half an unfolded length of the graft 10 as measured between ends of the legs 10a, 10b, such that the legs 10a, 10b of the graft 10 protrude from the access tunnel 50 when the graft 10 is fully pushed into the cavity 20. The width w and the depth d can vary at different portions of the bone cavity 20, as will be appreciated by a person skilled in the art. While the cavity can vary in size, in an exemplary embodiment, a width w of the cavity can be in a range of about 10 mm to 15 mm, e.g., about 10 mm to 13 mm, and a depth d of the cavity can be in a range of about 10 mm to 30 mm. The width w of the bone cavity 20 can define a maximum diameter of the bone cavity 20. As discussed above, various tools can be used to create a cavity having different sizes and shapes. In one embodiment, a bone cavity can have a substantially spherical shape such that the cavity's maximum depth and maximum width can be substantially equal and thus each define a maximum diameter of the cavity. In another embodiment, a bone cavity can have a box shape, e.g., having a substantially rectangular cross-sectional shape, with the cavity's width defining a maximum diameter of the cavity. A bone cavity can have a box-shape in the form of a cube such that the cavity's depth and width are substantially equal and thus each define a maximum diameter of the cavity. In yet another embodiment, a bone cavity can have an irregular shape, with the cavity's width defining a maximum diameter of the cavity.

In an exemplary embodiment, the cavity can have a width that is greater than a width t of the access tunnel. As shown in FIG. 1, the access tunnel 50 has a width t that is less than a width w of the cavity 20. In some embodiments, the width of the cavity can be in a range of about 20 to 100%, e.g., about 20 to 50%, greater than the width of the access tunnel. The length of the access tunnel can also vary and will depend on the location of the cavity within the bone. The size of the access tunnel can vary in different embodiments, but in an exemplary embodiment, the width t of the access tunnel can be in a range of about 6 mm to 12 mm, e.g., about 8 mm to 10 mm. The width t can vary at different portions of the access tunnel, as will be appreciated by a person skilled in the art. The width t of the access tunnel can define a maximum diameter of the access tunnel. In embodiments that have multiple access tunnels, the access tunnels can each have the same width and length, or they can have varying widths and lengths. The access tunnel can have a variety of shapes, such as substantially cylindrical as in the illustrated embodiment. In another embodiment, the access tunnel can have an irregular shape or a rectangular shape.

As indicated above, the tunnel and cavity are configured to receive a graft. Various grafts can be used based on the patient, the size and the shape of the damaged tissue, and other factors. By way of non-limiting example, tendon or ligament grafts formed from autologous tissue harvested from elsewhere in the body can be used, as well as allografts, artificial grafts, or tissue-engineered living replacements. Generally, a folded graft can range from 5 mm to 12 mm thick and from 80 mm to 120 mm long.

As mentioned above, a hardenable filler material in a first state can be placed into a cavity after a graft, such that when the hardenable filler material changes from the first state to a second, harder state, it can hold the part of the graft within the cavity against the bone, fixing the graft within the cavity. Various materials can be used as the hardenable filler material, for example a biocompatible material, such as a bone cement. The hardenable filler material can be sterile. The hardenable filler material can also be partially, fully, or non-bioabsorbable. Fully or partially bioabsorbable hardenable filler materials can include tricalcium phosphate (i.e., TCP). The hardenable filler material can be a homogeneous material or it can be formed from a combination of materials, such as a separate cement material and a hardening agent, for example. The hardenable filler material can be activated either just prior to or after the material is inserted into bone to change from the first state to the second state. The hardenable filler material can also be activated using various techniques, such as by combination with a hardening agent, combination with water, exposure to air, change in temperature, such as body temperature, or time, by way of non-limiting example. One example of a hardenable material that can be used is the CONFIDENCE SPINAL CEMENT SYSTEM™, offered by DePuy Spine, Inc., which hardens in approximately 15 minutes and achieves constant viscosity within approximately 8 to 10 minutes. An amount of hardenable filler material can be placed into the cavity such that, upon activation to the second harder state, the amount of hardener filler material has a size that prevents the material from passing through the access tunnel. The amount of hardenable filler can vary, for example, depending on the size of the cavity and the width of the access tunnel(s).

The hardenable filler material can be placed directly into the cavity or, alternatively, it can be placed into a balloon or sac 40, for example, as shown in FIG. 1. Alternatively, the hardenable filler material can come pre-packaged in the sac. The sac can be made from various flexible materials. By way of non-limiting example, the sac can be made from a woven material that is permeable to gases, such as air, but substantially impermeable to liquids or thick liquids, such as bone cement. The sac can be flexible such that its outer shape can adapt to the shape of the cavity. As the cavity can have a width that is greater than a width of the access tunnel, the outer shape of the sac can adapt such that it has a width greater than the width of the access tunnel. Such a configuration will prevent the sac from passing through the tunnel once the hardenable filler material hardens. The sac can have a fixed volume, or alternatively it can be expandable. The sac can be pre-filled with hardenable filler material prior to being inserted into the cavity, or alternatively it can be partially or fully filled before or after the sac is inserted into the cavity. The sac can have one or more discrete internal compartments (not shown), for example, to separate the hardenable filler material from a hardening agent or other material or liquid, such as water. In some embodiments, the discrete internal compartments can be configured to rupture or be punctured, such that their contents can be mixed. In other embodiments, the discrete internal compartments can remain intact. In some embodiments, the sac itself can be configured to rupture. In some embodiments the sac can be fully enclosed, or the sac can include an opening or a needle-penetrable area for allowing material to be delivered into the sac. In one embodiment, the sac can be open, like a bag. In the embodiments having an open sac, the sac can be sealable, or alternatively, it can remain open. The sac can be formed from various biocompatible materials. The sac can be sterile. In some embodiments, the sac can also be partially or fully bioabsorbable, whereas in other embodiments, it is non-absorbable. Sacs of various sizes and shapes can be used, depending on various factors, such as the cavity size and graft size, for example. A combination sac and implant can also be used, as described more fully below. A person skilled in the art will appreciate that a variety of other housings or carriers can be used to deliver and/or contain the hardenable filler material.

Figure 2:
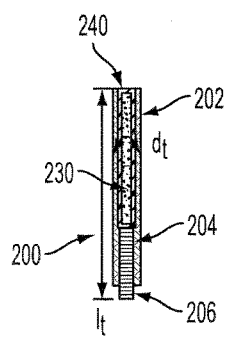
FIG. 2 is a cross-sectional view of one embodiment of a delivery tool.
Figure 3:
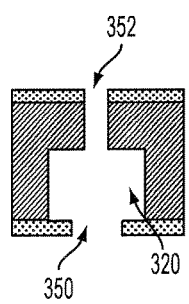
FIG. 3 is a cross-sectional view of one embodiment of a bone cavity.
Figure 4:
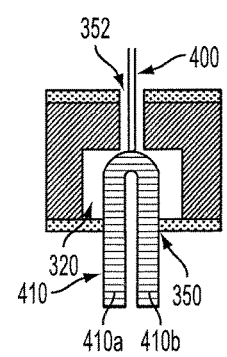
FIG. 4 is a cross-sectional view of a graft partially inserted into the bone cavity of FIG. 3.

The hardenable filler material can be placed in the cavity or in the sac by various methods and delivery tools, including, by way of non-limiting example, extruders and syringes. FIG. 2 illustrates one embodiment of a delivery tool 200 having an outer tube 202 defining an inner lumen 204, and a piston 206 slidably disposed therein. The piston 206 can slide proximally and distally to alternately increase and decrease the space within the inner lumen 204 and push any material disposed within the lumen 204 out of the delivery tool 200. In some embodiments, as discussed further below, the tool can have an inner tube with an open sac attached to one end. The inner tube can be disposed within a removable outer tube and the piston can be disposed within the inner tube. The outer tube can be removed in various ways, for example, by sliding the outer tube proximally over the inner tube and out from the access tunnel. The size of the delivery tool can vary, depending on the width of the access tunnel and the length required to access the bone cavity. The size of the piston can also vary, for example, the piston can be the same length as the tube in which it is disposed, whereas in other embodiments, it can be shorter or longer than the tube.

One exemplary method of fixing a graft within a bone cavity is illustrated by FIGS. 2-7. In this embodiment, a sac 240 filled with hardenable filler material 230 can be loaded into the delivery tool 200. The piston 206 can be slid out of the inner lumen 204 such that the sac 240 can be substantially contained within the inner lumen 204 of the delivery tool 200.

First and second access tunnels 350, 352 can be drilled through opposite sides of a bone, such as the femur, to thereby form two tunnels extending through cortical bone. The first access tunnel 350 can be wider than the second access tunnel 352, while the second access tunnel can be longer and can extend through cancellous bone as well as cortical bone. A cavity 320 can be formed within the cancellous bone between the two bone tunnels 350, 352. The cavity can have a width that is greater than a width of each bone tunnel. A central folded portion of a graft 410 can be inserted into the bone cavity 320 through the first access tunnel 350 such that the legs 410a, 410b of the graft protrude out from the access tunnel 350. The graft 410 can be attached to a suture 400 at any point along the graft 410, but preferably a suture is attached at the fold such that the suture 400 can be used to pull the graft 410 into the bone cavity 320, with the ends of the graft 410a, 410b extending out through the access tunnel 350. In particular, the suture can be passed through the first access tunnel 350, through the cavity 320, and through the second access tunnel 352. The suture 400 can be pulled to thereby pull the graft 410 through the first access tunnel 350 and into the cavity 320. The reduced width of the second access tunnel 352 can prevent the graft 410 from being pulled through the second access tunnel 352. While the graft 410 can be pulled into the bone cavity 320 by the suture 400, in other embodiments, the graft can be pushed into the bone cavity 320 through the first access tunnel 350.

Figure 5:
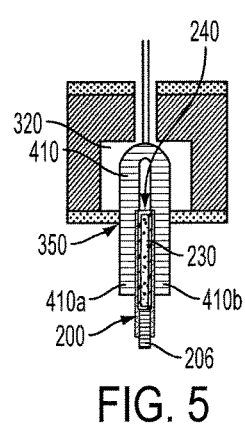
FIG. 5 is a cross-sectional view of the delivery tool of FIG. 2 loaded with a sac of hardenable filler material partially inserted into the graft of FIG. 4.

As shown in FIG. 5, with the graft 410 positioned in the first access tunnel 350, the delivery tool 200 can be at least partially inserted between the ends of the graft 410a, 410b into the first access tunnel 350. The piston 206 can be advanced further into the delivery tool 200 such that the sac 240 filled with hardenable filler material 230 is forced out of the delivery tool 200 and delivered into the bone cavity 320 towards the central portion of the graft 410. As mentioned above, the sac 240 and the hardenable filler material 230 can be sterile. Prior to activation, the hardenable filler material remains in a viscous first state. The sac can adapt its shape to the bone cavity. For example, the sac 240 can adapt to the cavity 320 such that the sac 240 has a width that is greater than the width of the access tunnel t. Expansion of the sac within the cavity will push the graft into contact with the inner walls of the cavity, i.e., with the bone. The hardenable filler material 230 can then be activated to move from its first state to a second hardened state. After the hardenable filler material 230 is activated to its second, harder state, the sac 240 can firmly compress portions of the graft 410 against walls of the bone cavity 320. The sac 240 containing the hardenable filler material 230 in the second state can have a fixed width that is greater than the width of the access tunnel t, such that the sac 240 and the graft 410 are fixed within the bone cavity 320 by interference and cannot be easily removed through the first access tunnel 350 or the second access tunnel 352, as shown in FIG. 6.

The hardenable filler material can be activated in several ways, as mentioned above. For example, the sac 240 prefilled with hardenable filler material 230 can have a plurality of discrete internal compartments (not shown) configured to rupture in response to a threshold pressure placed on the sac 240. Each compartment can hold one or more separate ingredients of a hardenable filler material. For example, a first compartment can contain a first ingredient, such as a viscous bone cement and a second compartment can contain a second material, such as a hardening agent or an activator (e.g., water). A threshold pressure can be placed on the sac 240 just prior to inserting the sac 240 into the bone cavity 320, such that the threshold pressure ruptures the first and second compartments causing the first and second ingredients to mix together and activate the hardenable bone filler material to a second, harder state. The threshold pressure can be placed on the sac 240 before or after the sac 240 is loaded into the delivery tool 200. In some embodiments, the threshold pressure can be placed on the sac after the sac 240 is inserted into the bone cavity 320, for example, by a wall of the bone cavity 320. In some embodiments, the hardenable filler material can be activated by mixing ingredients or by combining with a hardening agent or an activator in a single compartment within the sac, a syringe or other carriers or housings. In some embodiments, the hardenable filler material changes from the first viscous state to the second, harder state within a period of time, whereas in other embodiments, the hardenable filler material changes from the first state to the second state substantially instantaneously upon activation. The period of time can vary range in the range of about 3 minutes to 30 minutes, and more preferably in the range of about 10 minutes to 20 minutes.

After the sac 240 is delivered into the bone cavity 320, and prior to or after activation of the hardenable filler material 230, the delivery tool 200 can be withdrawn from within the folded graft 410 and from the first access tunnel 350. While the delivery tool 200 can be removed at any time after the sac 240 is delivered into the bone cavity 320, preferably the delivery tool 200 is removed after the hardenable filler material 230 is activated to its second, harder state. This will prevent the hardenable filler material 230 and the sac 240 from hardening in the first access tunnel 350. The ends 410a, 410b of the graft 410 can passively come together, or alternatively, they can be whipstitched together, manually pressed together, or otherwise positioned.

Another exemplary method of fixing a graft within a bone cavity is illustrated by FIGS. 8-14. In this embodiment, as illustrated in FIG. 8, the delivery tool 800 can have an outer tube 802, an inner tube 803, and a piston 806. The inner tube 803 can be disposed within an inner lumen 804 defined by the outer tube 802. The piston 806 can be slidably disposed within a proximal end of the inner tube 803, while an open sac 840 can be attached to the distal end of the inner tube 803. The sac 840 can be contained within the outer tube 802 for delivery into a bone cavity. The inner lumen 804 of the inner tube 803 can be loaded with a hardenable filler material 830, such that slidable movement of the piston 806 distally will push the hardenable filler material 830 into the open sac 840 causing the sac to become filled. In this embodiment, the sac 840 can preferably be permeable to gases, such as air, so that residual air does not become trapped within the sac 840.

A graft 1010 with a suture 1000 attached thereto can be inserted into a bone cavity 920 located between two access tunnels 950, 952, as illustrated by FIGS. 9 and 10. The trailing ends of the graft 1010a, 1010b can extend through the first access tunnel 950 and the suture 1000 can extend through the opposite second access tunnel 952. The folded portion of the graft can be seated within the cavity. The delivery tool 800 can be inserted between the trailing ends 1010a, 1010b of the graft 1010 such that the portion of the tool containing the sac 840 is within the bone cavity 920, as shown in FIG. 11. As illustrated in FIG. 12, once the delivery tool 800 is situated within the first access tunnel 952 and between the legs 1010a, 1010b of the graft 1010, the outer tube 802 of the delivery tool 800 can be removed leaving the sac 840 inside the cavity 920 and within the graft 1010. The piston 806 can be advanced through the inner tube 803 such that the hardenable filler material 830 is delivered into the open sac 840, which expands to conform to the shape of the bone cavity 920, as shown in FIG. 13. As a result, after the hardenable filler material 830 is activated from its first state to its second, harder state, the delivery tool 800 can be removed from within the graft 1010, for example, by shearing, twisting, or breaking off the inner tube 803 from the open sac 840. In this embodiment, the open sac 840 remains open and unsealed, as illustrated in FIG. 14, however a person skilled in the art will appreciate that the sac can be sealed or closed using various techniques.

Another exemplary method of fixing a graft within a bone cavity is illustrated by FIGS. 15-21. As shown in FIG. 15, in this embodiment the graft 1510 contains an open sac 1540 positioned therein, with the graft 1510 folded around the sac 1540 and ends 1510a, 1510b of the graft 1510 whipstitched together to secure the sac 1540 therein. The sac 1540 can include a neck 1542 that is threaded through the folded portion of the graft 1510. A bone cavity 1620 can be formed, as shown in FIG. 16, with first and second access tunnels 1650, 1652. The graft 1510 can be inserted into the bone cavity 1620 such that the ends 1510a, 1510b of the graft extend through the first access tunnel 1650 and the neck 1542 of the sac 1540 extends through the second access tunnel 1652, as illustrated in FIG. 17. The neck 1542 of the sac 1540 can be pulled such that the graft 1510 abuts the access tunnel 1652. A syringe 1800 containing hardenable filler material 1830 can be inserted into the neck 1542 of the sac 1540, as shown in FIG. 18. The hardenable filler material 1830 can be injected into the sac 1540 from the syringe 1800, expanding the sac 1540 within the graft 1510 and causing the sac 1540 to compress the graft 1510 against the walls of the bone cavity 1620, as shown in FIG. 19. As illustrated in FIG. 20, the hardenable filler material 1830 can be activated from a first viscous state to a second harder state. The syringe 1800 can be removed before or after the hardenable filler material 1830 is activated. The neck 1542 of the sac 1540 can be trimmed to a desired length, for example, such that it does not extend past the bone, as shown in FIG. 21.

Another exemplary method of fixing a graft within a bone cavity is illustrated by FIGS. 22-27. As with the previous embodiment, this embodiment can contain an empty open sac 2240 contained within a graft 2210, as illustrated by FIG. 22. The open sac 2240 can be connected to a detachable tube 2244 that extends through the folded portion of the graft 2210 such that the tube 2244 is in communication with the inner lumen in the sac 2240. A bone cavity 2320 can be created with first and second access tunnels 2350, 2352, as shown in FIG. 23, and the graft 2210 and sac 2240 can be placed within the bone cavity 2320 such that the ends 2210a, 2210b of the graft 2210 extend through the first access tunnel 2350 and the detachable tube 2244 extends through the second access tunnel 2352, as shown in FIG. 24. The tube 2244 can optionally be used to pull the graft into the cavity 2320. A syringe 2500 containing hardenable filler material 2530 can be attached to an end of the detachable tube 2244 that is outside of the bone cavity 2320, as illustrated in FIG. 25. The hardenable filler material 2530 can be injected from the syringe 2500 through the detachable tube 2244 into the sac 2240, causing the sac 2240 to expand and compress the graft 2210 against the walls of the bone cavity 2320, as illustrated by FIG. 26. Before or after the hardenable filler material 2530 is activated from a first viscous state to a second harder state, the detachable tube 2244 can be broken or sheared off from the sac 2240 and removed from the second access tunnel 2352, as shown in FIG. 27.

Figure 28:
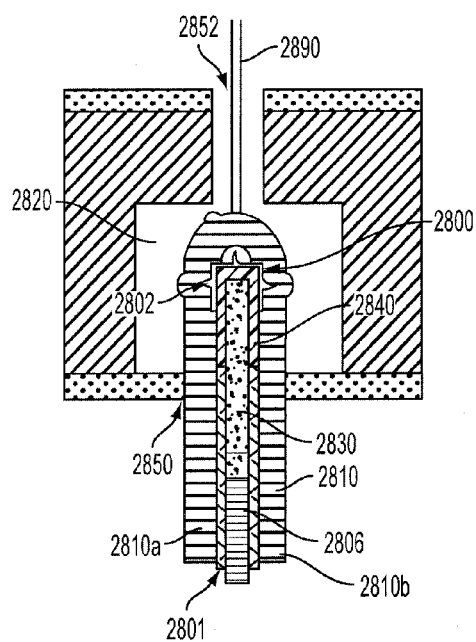
FIG. 28 is a cross-sectional view of an embodiment of a graft and an open sac attached to a biocompatible structure having anchoring elements partially inserted into a bone cavity.
Figure 29:
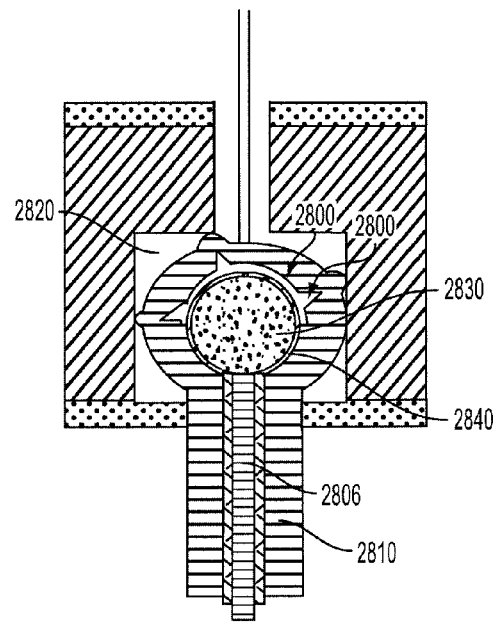
FIG. 29 is a cross-sectional view of the graft of FIG. 28 being anchored to the bone cavity by the anchoring elements.

Another exemplary method of fixing a graft within a bone cavity is illustrated in FIGS. 28-29. In this embodiment, a combination sac and implant can be used. A biocompatible structure, for example, poly-ether-ether-ketone (PEEK), with anchoring elements, such as ribs, spikes, or other surface features or protrusions can be attached to or formed on an outside surface of the sac. FIG. 28 illustrates one example of a biocompatible structure 2800 with a plurality of anchoring elements 2802 on the outside of a sac 2840. Though this embodiment shows the biocompatible structure 2800 partially covering the sac 2840, it will be understood that the biocompatible structure can entirely cover the sac or cover various portions thereof. The biocompatible structure can have a fixed size, or, alternatively, it can be flexible and/or expandable to adjust to the shape of the sac. In embodiments with a rigid biocompatible structure, the shape of the biocompatible structure can determine the shape of the sac in an expanded configuration. For example, a biocompatible structure can have a rigid semi-spherical shape, and the portion of the sac attached thereto will have a semi-spherical shape when expanded. In another example, the rigid biocompatible structure can have openings or windows, and the portion of the sac attached thereto can push through the windows when expanded. The biocompatible structure can be attached to the sac either before or after insertion of the sac and the biocompatible structure into the bone cavity. The biocompatible structure can have one or more anchoring elements, and the anchoring elements can be of the same type, or various types of anchoring elements can be used on the same biocompatible structure. The biocompatible structures disclosed herein can be formed from various biocompatible materials, including, by way of non-limiting example, surgical grade titanium, and polymers, such as poly-ether-ether-ketone (PEEK), polylactic acid, polyglycolic acid, and combinations thereof.

The sac 2840 can be attached to a distal end of an inner tube 2803 of a delivery tool 2801. Though delivery tool 2801 is shown without a removable outer tube, in some embodiments, the delivery tool can have a removable outer tube for retaining the sac during delivery, as discussed above. A piston 2806 can be slidably disposed within a proximal end of the inner tube 2803. An inner lumen of the inner tube 2803 can be loaded with a hardenable filler material 2830, such that slidable movement of the piston 2806 distally will push the hardenable filler material 2830 into the open sac 2840 causing the sac to become filled. In this embodiment, the sac 2840 can preferably be permeable to gases, such as air, so that residual air does not become trapped within the sac 2840.

As illustrated by FIG. 28, a graft 2810 with a suture 2890 attached can be inserted into a bone cavity 2820 that is created with two access tunnels 2850, 2852, as previously described. The folded portion of the graft can be seated within the cavity. The delivery tool 2801 can be inserted between trailing ends 2810a, 2810b of the graft 2810 such that the portion of the tool 2801 containing the sac 2840 is within the bone cavity 2820, as shown in FIG. 28. As shown in FIG. 29, once the delivery tool 2801 is situated within the first access tunnel 2850 and between the legs 2810a, 2810b of the graft 2810, the piston 2806 can be advanced distally through the inner tube 2803 to eject the hardenable filler material 2830 into the sac 2840 such that it expands and compresses the graft 2810 against the walls of the bone cavity 2820. Expansion of the sac 2840 will also cause the anchoring elements 2802 on the biocompatible structure 2800 to extend into and engage the graft 2810, thereby preventing slidable motion of the graft 2810. After the hardenable filler material 2830 is activated from a first viscous state to a second harder state, the anchoring elements 2802 will thus anchor the graft 2810 to the sac 2840. The anchoring elements 2802 can be used to control the positioning of the graft 2810, for example, the anchoring elements 2802 can be separated and oriented such that anchoring elements separate the graft 2810 into separate sections or "bundles" of fibers and effectively achieve an anatomical double bundle. In some methods, this orientation can be advantageous because a double bundle of the graft can more accurately represent certain natural tissues, such as, for example, the anterior cruciate ligament, which has two functional bundles.

Once a graft is anchored to the bone as illustrated in the previous embodiments, for example, as graft 2810 is anchored within bone cavity 2820, the trailing ends 2810*a*, 2810*b* of the graft 2810 can be anchored, as well. For example, the ends 2810*a*, 2810*b* of the graft 2810 can be anchored to tissue or bone in any number of ways, including being anchored in a second cavity using the methods and devices disclosed herein. By way of non-limiting example, one or both ends 2810*a*, 2810*b* of the graft 2810 can be anchored using an anchor, a hardenable bone filler material, adhesive, or a suture. The suture 2890 attached to the folded portion of the graft 2810 may also be used to anchor the graft 2810, for example, to the bone. In other embodiments, the trailing ends of the graft can be attached to tissue, either directly or using a suture, to anchor the tissue to bone.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical kit, comprising: a graft; a flexible sac having an unexpanded configuration and an expanded configuration, the flexible sac being disposed in an internal pocket of the graft in the unexpanded configuration, the graft and the flexible sac being configured to be advanced as a unit into a cavity formed in bone; a hardenable filler material having a first state and a second, harder state, the hardenable filler material being configured to be inserted in the first state into the flexible sac positioned in the internal pocket of the graft, thereby causing the flexible sac to move from the unexpanded configuration to the expanded configuration and causing the internal pocket to move from a first size to a second, larger size to cause the graft to contact and push against walls of the cavity such that when the hardenable filler material changes from the first state to the second, harder state in the internal pocket, the graft is held in contact against the walls of the cavity; and a tube coupled to the flexible sac and being configured to be pulled so as to advance the graft and the flexible sac as the unit into the cavity.

2. The kit of claim 1, wherein the tube has an inner lumen extending therethrough in fluid communication with an interior of the flexible sac, the hardenable filler material being configured to be advanced through the inner lumen in the first state into the interior of the flexible sac.

3. The kit of claim 1, wherein the tube is configured to be detached form the flexible sac after being pulled to advance the graft and the flexible sac as the unit into the cavity.

4. The kit of claim 1, wherein the flexible sac is sterile and the hardenable filler material is sterile.

5. The kit of claim 1, wherein the flexible sac includes a single internal cavity, the hardenable filler material being configured to be contained within the single internal cavity.

6. The kit of claim 1, wherein the flexible sac includes first and second discrete internal compartments therein, the first internal compartment being configured to contain the hardenable filler material therein, and the second internal compartment being configured to contain a second, different material therein.

7. The kit of claim 1, wherein the flexible sac has an opening formed therein, and the hardenable filler material is configured to be inserted in the first state through the opening and into the flexible sac positioned in the internal pocket of the graft.

8. The kit of claim 1, wherein the graft is folded, and the flexible sac is disposed within a pocket formed by the fold.

9. A surgical kit, comprising: a graft; a flexible sac having an unexpanded configuration and an expanded configuration, the flexible sac being disposed in an internal pocket of the graft in the unexpanded configuration, the graft and the flexible sac being configured to be advanced as a unit into a cavity formed in bone; a hardenable filler material having a first state and a second, harder state, the hardenable filler material being configured to be inserted in the first state into the flexible sac positioned in the internal pocket of the graft, thereby causing the flexible sac to move from the unexpanded configuration to the expanded configuration and causing the internal pocket to move from a first size to a second, larger size to cause the graft to contact and push against walls of the cavity such that when the hardenable filler material changes from the first state to the second, harder state in the internal pocket, the graft is held in contact against the walls of the cavity, wherein the graft and the flexible sac are configured to be advanced as the unit into the cavity formed in bone such that a neck of the flexible sac extends through a bone tunnel providing access to the cavity, and the hardenable filler material is configured to be inserted in the first state through the neck and into the flexible sac positioned in the internal pocket of the graft.

10. The kit of claim 9, wherein the graft and the flexible sac are configured to be advanced as the unit into the cavity formed in bone by pulling the neck of the flexible sac through the bone tunnel.

11. The kit of claim 10, wherein the graft and the flexible sac are configured to be advanced as the unit into the cavity through a second bone tunnel providing access to the cavity as the neck is being pulled.

* * * * *